United States Patent [19]

Eicken et al.

[11] 4,373,945
[45] Feb. 15, 1983

[54] HERBICIDAL AGENTS BASED ON ACETANILIDES

[75] Inventors: Karl Eicken, Wachenheim; Bruno Wuerzer, Limburgerhof, both of Fed. Rep. of Germany

[73] Assignee: BASF Aktiengesellschaft, Fed. Rep. of Germany

[21] Appl. No.: 209,961

[22] Filed: Nov. 24, 1980

Related U.S. Application Data

[62] Division of Ser. No. 56,146, Jul. 9, 1979, Pat. No. 4,277,278.

[30] Foreign Application Priority Data

Jul. 21, 1978 [DE] Fed. Rep. of Germany ....... 2832046

[51] Int. Cl.$^3$ .............................................. A01N 43/26
[52] U.S. Cl. ........................................................ 71/92
[58] Field of Search .............................................. 71/92

[56] References Cited

U.S. PATENT DOCUMENTS 4,277,278 7/1981 Eicken et al. ........................ 71/92

Primary Examiner—Paul M. Coughlan, Jr.
Attorney, Agent, or Firm—Keil & Witherspoon

[57] ABSTRACT

Herbicidal agents containing an N-azolylmethyl-haloacetanilide of the formula

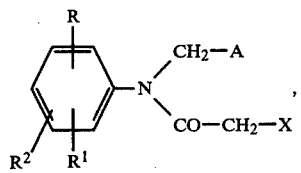

where R denotes hydrogen or linear or branched alkyl or alkoxy of a maximum of 5 carbon atoms, $R^1$ denotes hydrogen, halogen, or linear or branched alkyl or alkoxy of a maximum of 5 carbon atoms, $R^2$ denotes hydrogen, halogen, or linear or branched alkyl or alkoxy of a maximum of 5 carbon atoms, R together with $R^2$ forms an alkylene chain of a maximum of 6 carbon atoms which is linked in the o-position and is unsubstituted or substituted by linear alkyl of a maximum of 4 carbon atoms, X denotes chlorine or bromine, and A denotes an azole which is attached via a ring nitrogen atom and is unsubstituted or mono- or poly-substituted by halogen, phenyl, alkyl, alkoxy, alkylthio or perfluoroalkyl, each of a maximum of 4 carbon atoms, cyano, carboxy, carbalkoxy of a maximum of 4 carbon atoms in the alkoxy, or alkanoyl of a maximum of 4 carbon atoms, A also denoting a salt of an azole containing 2 or 3 nitrogen atoms, and a haloacetanilide of the formula

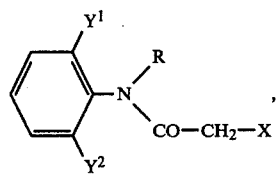

where R denotes linear or branched alkyl, alkenyl or alkynyl, each of a maximum of 4 carbon atoms, or —A—$R^1$, A denoting alkylene of 1 or 2 carbon atoms which may be monosubstituted by ethyl or mono- or disubstituted by methyl, and $R^1$ denoting linear or branched alkoxy, haloalkoxy, alkenoxy, alkynoxy or alkoxyalkoxy, each of a maximum of 4 carbon atoms, cycloalkoxy or cycloalkylmethoxy with 3 to 6 carbon atoms in the cycloalkyl ring, 1,3-dioxolan-2-yl or alkoxycarbonyl of a maximum of 4 carbon atoms in the alkoxy, X denotes chlorine or bromine, and $Y^1$ and $Y^2$ are identical or different and each denotes hydrogen or linear or branched alkyl of a maximum of 4 carbon atoms, $Y^1$ and $Y^2$ only denoting hydrogen when R is linear or branched alkyl, alkenyl or alkynyl, each of a maximum of 4 carbon atoms.

The ratio of N-azolylmethylhaloacetanilide of the formula I to haloacetanilide of the formula II is from 1:0.5 to 1:20 parts by weight.

2 Claims, No Drawings

HERBICIDAL AGENTS BASED ON ACETANILIDES

This is a division of application Ser. No. 056,146 filed July 9, 1979 now U.S. Pat. No. 4,277,278.

The present invention relates to herbicidal agents containing mixtures of haloacetanilides, and a process for controlling the growth of unwanted plants with these herbicidal agents.

German Pat. No. 1,014,380, U.S. Pat. Nos. 3,442,945, 3,547,620 and German Laid-Open Application DE-OS No. 2,328,340 disclose that haloacetanilides are herbicidally effective. In particular, chloroacetanilides in which the phenyl ring is unsubstituted, or in which the phenyl ring bears alkyl substituents in the 2- and 6-positions, are suitable for controlling unwanted grasses. For instance, 2-chloro-N-isopropylacetanilide is used as a herbicide in Indian corn, sorghum, soybeans and onions, 2-chloro-2',6'-diethyl-N-methoxymethylacetanilide as a herbicide in Indian corn, soybeans and rape, and 2-chloro-2'-ethyl-6'-methyl-N-(1'-methoxyprop-2'-yl)-acetanilide as as herbicide in Indian corn, soybeans, sugarbeets and other crops.

These chloroacetanilides are predominantly suitable for removing unwanted grasses of the Setaria, Digitaria, Eleusine and Echinochloa genera. Other agriculturally important grasses such as Alopecurus, Bromus and Brachiaria species, or Sorghum halepense, are combated less well. Of the broadleaved (dicotyledonous) plants, only Amaranthus and a few other species are checked relatively well.

By comparison, the haloacetanilides disclosed in German Laid-Open Application DE-OS No. 2,648,008 and which bear on the nitrogen unsubstituted or substituted azolylmethyl linked via a ring nitrogen atom, such as pyrazol-1-yl-methyl, triazol-1-yl-methyl or tetrazol-1-yl-methyl, have, at low application rates, not only an excellent herbicidal action on grasses but also a good action on broadleaved species.

Further, U.S. Pat. No. 3,422,945 and German Laid-Open Application DE-OS No. 2,328,340 disclose that the haloacetanilides described therein may also be used in combination with other herbicidal active ingredients, e.g., certain other acetanilides; however, no details are given on the direction and degree of action of these combinations.

We have now found that herbicidal agents which contain a mixture of an N-azolylmethylhaloacetanilide of the formula

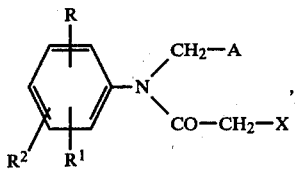

where R denotes hydrogen or linear or branched alkyl or alkoxy of a maximum of 5 carbon atoms, $R^1$ denotes hydrogen, halogen, or linear or branched alkyl or alkoxy of a maximum of 5 carbon atoms, $R^2$ denotes hydrogen, halogen, or linear or branched alkyl or alkoxy of a maximum of 5 carbon atoms, R together with $R^2$ forms an alkylene chain of a maximum of 6 carbon atoms which is linked in the o-position and is unsubstituted or substituted by linear alkyl of a maximum of 4 carbon atoms, X denotes chlorine or bromine, and A denotes an azole which is attached via a ring nitrogen atom and is unsubstituted or mono- or polysubstituted by halogen, phenyl, alkyl, alkoxy, alkylthio or perfluoroalkyl, each of a maximum of 4 carbon atoms, cyano, carboxy, carbalkoxy of a maximum of 4 carbon atoms in the alkoxy, or alkanoyl of a maximum of 4 carbon atoms, A also denoting a salt of an azole containing 2 or 3 nitrogen atoms, and a haloacetanilide of the formula

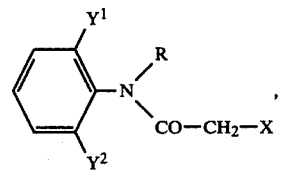

where R denotes linear or branched alkyl, alkenyl or alkynyl, each of a maximum of 4 carbon atoms, or —A—$R^1$, A denoting alkylene of 1 or 2 carbon atoms which may be monosubstituted by ethyl or mono- or disubstituted by methyl, and $R^1$ denoting linear or branched alkoxy, haloalkoxy, alkenoxy, alkynoxy or alkoxyalkoxy, each of a maximum of 4 carbon atoms, cycloalkoxy or cycloalkylmethoxy with 3 to 6 carbon atoms in the cycloalkyl ring, 1,3-dioxolan-2-yl or alkoxycarbonyl of a maximum of 4 carbon atoms in the alkoxy, X denotes chlorine or bromine, and $Y^1$ and $Y^2$ are identical or different and each denotes hydrogen or linear or branched alkyl of a maximum of 4 carbon atoms, $Y^1$ and $Y^2$ only denoting hydrogen when R is linear or branched alkyl, alkenyl or alkynyl, each of a maximum of 4 carbon atoms, have a more intensive and a wider range of action than herbicidal agents containing only a haloacetanilide of the formula I or of the formula II. Surprisingly, the haloacetanilides of the formula I and II in these mixtures have a distinct synergistic action, particularly at application rates at which one or both mixture components exhibit an insufficient action.

Suitable components of the formula I are N-azolylmethylhaloacetanilides in which R is hydrogen, alkyl of a maximum of 5 carbon atoms, such as methyl, ethyl, n-propyl, isopropyl, n-butyl, sec-butyl, isobutyl, tert-butyl, linear and branched pentyl, and alkoxy of a maximum of 5 carbon atoms, such as methoxy, ethoxy, propoxy, butoxy and pentoxy;

$R^1$ and $R^2$ are hydrogen, halogen, such as fluorine, chlorine, bromine and iodine, alkyl of a maximum of 5 carbon atoms, such as methyl, ethyl, n-propyl, isopropyl, n-butyl, sec-butyl, iso-butyl, tert-butyl, linear and branched pentyl, alkoxy of a maximum of 5 carbon atoms, such as methoxy, ethoxy, propoxy, butoxy, and pentoxy; R together with $R^2$ is an alkylene chain of a maximum of 6 carbon atoms, linked in the o-position and unsubstituted or substituted by alkyl of a maximum of 4 carbon atoms, e.g., ethylene, trimethylene, tetramethylene, 1-methyltrimethylene, 1,1-dimethyltrimethylene, and 1,1-dimethyltetramethylene; X is chlorine, bromine or iodine, preferably chlorine; and A is an azole attached via a ring nitrogen atom, e.g., pyrrole, pyrazole, imidazole, 1,2,4-triazole, 1,2,3-triazole, and tetrazole, which is unsubstituted or mono- or polysubstituted by halogen, phenyl, alkyl, alkoxy, alkylthio or perfluoroalkyl, each of a maximum of 4 carbon atoms, cyano, carboxy, carbalkoxy of a maximum of 4 carbon atoms in the alkoxy, or alkanoyl of a maximum of 4 carbon atoms, the substituents being identical or different, such as 2,6-dimethylpyrrole, tetramethylpyrrole, 3(5)-methylpyrazole, 4-methylpyrazole, 3(5)-ethylpyrazole, 4-ethylpyrazole, 3(5)-iso-propylpyrazole, 4-isopropylpyrazole, 3,5-dimethylpyrazole, 3,5-dimethyl-4-acetylpyrazole, 3,5-dimethyl-4-propionylpyrazole, 3,4,5-trimethylpyrazole, 3(5)-phenylpyrazole, 4-phenylpyrazole, 3,5-diphenylpyrazole, 3(5)-phenyl-5(3)-methylpyrazole, 3(5)-chloropyrazole, 4-chloropyrazole, 4-bromopyrazole, 4-iodopyrazole, 3,4,5-trichloropyrazole, 3,4,5-tribromopyrazole, 3,5-dimethyl-4-chloropyrazole, 3,5-dimethyl-4-bromopyrazole, 4-chloro-3(5)-methylpyrazole, 4-bromo-3(5)-methylpyrazole, 4-methyl-3,5-dichloropyrazole, 3(5)-methyl-4,5(3)-dichloropyrazole, 3(5)-chloro-5(3)-methylpyrazole, 4-methoxypyrazole, 3(5)-methyl-5(3)-methoxypyrazole, 3(5)-ethoxy-4,5(3)-dimethylpyrazole, 3(5)-methyl-5(3) -trifluoromethylpyrazole, 3,5-bis-trifluoromethylpyrazole, 3(5)-methyl-5(3)-carbethoxypyrazole, 3,5-bis-carbethoxypyrazole, 3,4,5-triscarbethoxypyrazole, 3(5)-methyl-5(3)-methylthio-4-carbethoxypyrazole, 4-methyl-3,5-bis-carbethoxypyrazole, 4-cyanopyrazole, 4-methoxy-3,5-dichloropyrazole, 4,5-dichloroimidazole, 2-methyl-4,5-dichloroimidazole, 2-ethyl-4,5-dichloroimidazole, 3(5)-methyl-1,2,4-triazole, 3,5-dimethyl-1,2,4-triazole, 3(5)-chloro-1,2,4-triazole, 3(5)-bromo-1,2,4-triazole, 3(5)-chloro-5(3)-methyl-1,2,4-triazole, 3,5-dichloro-1,2,4-triazole, 3,5-dibromo-1,2,4-triazole, 3(5)-chloro-5(3)-cyano-1,2,4-triazole, 3(5)-chloro-5(3)-phenyl-1,2,4-triazole, 3(5)-chloro-5(3)-carbomethoxy-1,2,4-triazole, 3(5)-methylthio-1,2,4-triazole, 4(5)-methyl-1,2,3-triazole, 4,5-dimethyl-1,2,3-triazole, 4(5)-phenyl-1,2,3-triazole, 4(5)-chloro-1,2,3-triazole, 1,2,3-triazol-4(5)-ylcarboxylic acid ethyl ester, 1,2,3-triazol-4,5-yl-dicarboxylic acid dimethyl ester, 5-methyltetrazole, 5-chlorotetrazole, and tetrazolyl-5-carboxylic acid ethyl ester.

Furthermore, the radical A may, when the optionally substituted azole contains 2 or 3 nitrogen atoms, also be attached in a saltlike manner to one of the usual strong inorganic or organic acids, e.g., hydrochloric acid, hydrobromic acid, nitric acid, sulfuric acid, tetrafluoboric acid, fluosulfonic acid, and formic acid, a halogenated carboxylic acid, e.g., trichloroacetic acid, an alkanesulfonic acid, e.g., methanesulfonic acid, a halogenated alkanesulfonic acid, e.g., trifluoromethanesulfonic acid and perfluorohexanesulfonic acid, and an arylsulfonic acid, e.g. dodecylbenzenesulfonic acid.

Preferred acetanilides are those which bear methyl or ethyl in the 2- and 6-positions on the phenyl ring and hydrogen, methyl or ethyl in the 3-position; suitable azoles are pyrazole, triazole and tetrazole, each of which is unsubstituted or substituted by lower alkyl, alkoxy, carbalkoxy, cyano or halogen.

In particular, the herbicidal agents according to the invention contain the following N-azolylmethylhaloacetanilides: 2-chloro-2',6'-dimethyl-N-(pyrazol-1-yl-methyl)-acetanilide, 2-chloro-2'-methyl-6'-ethyl-N-(pyrazol-1-yl-methyl)-acetanilide, 2-chloro-2',6'-dimethyl-N-(4-methylpyrazol-1-yl-methyl)-acetanilide, 2-chloro-2'-methyl-6'-ethyl-N-(4-methoxypyrazol-1-yl-methyl)-acetanilide, 2-chloro-2'-methyl-6'-ethyl-N-(3(5)-methylpyrazol-1-yl)-acetanilide, 2-chloro-2',6'-dimethyl-N-(3,5-dimethylpyrazol-1-yl-methyl)-acetanilide, 2-chloro-2',6'-dimethyl-N-(1,2,4-triazol-1-yl-methyl)-acetanilide, 2-chloro-2',6'-dimethyl-N-(4-chloropyrazol-1-yl-methyl)-acetanilide, 2-chloro-2',3',6'-trimethyl-N-(pyrazol-1-yl-methyl)-acetanilide, 2-chloro-2'-methyl-6'-ethyl-N-(3,5-dimethylpyrazol-1-yl-methyl)-acetanilide, 2-chloro-2',6'-diethyl-N-(3,5-dimethylpyrazol-1-yl-methyl)-acetanilide, 2-chloro-2',3',6'-trimethyl-N-(3,5-dimethylpyrazol-1-yl-methyl)-acetanilide, 2-chloro-2',6'-diethyl-N-(4-methylpyrazol-1-yl-methyl)-acetanilide, 2-chloro-2'-methyl-6'-ethyl-N-(4-methylpyrazol-1-yl-methyl)-acetanilide, 2-chloro-2',3',6'-trimethyl-N-(4-methylpyrazol-1-yl-methyl)-acetanilide, 2-chloro-2',6'-dimethyl-N-(3-(5)-methylpyrazol-1-yl-methyl)-acetanilide, 2-chloro-2',6'-diethyl-N-(3-(5)-methylpyrazol-1-yl-methyl)-acetanilide, 2-chloro-2',6'-dimethyl-N-(4-methoxypyrazol-1-yl-methyl)-acetanilide, 2-chloro-2',6'-diethyl-N-(pyrazol-1-yl-methyl)-acetanilide, 2-chloro-2'-methyl-6'-ethyl-N-(1,2,4-triazol-1-yl-methyl)-acetanilide, 2-chloro-2',6'-diethyl-N-(1,2,4-triazol-1-yl-methyl)-acetanilide, 2-chloro-2',3',6'-trimethyl-N-(1,2,4-triazol-1-yl-methyl)-acetanilide, 2-bromo-2',6'-dimethyl-N-(pyrazol-1-yl-methyl)-acetanilide and 2-bromo-2'-methyl-6'-ethyl-N-(pyrazol-1-yl-methyl)-acetanilide.

The N-azolylmethylhaloacetanildes of the formula I, and the manufacture thereof, are disclosed in German Laid-Open Application DE-OS Nos. 2,648,008 and 2,744,396.

Suitable components of the formula II are haloacetanilides in which R denotes —A—$R^1$. For instance, R may denote —$CH_2$—O—Z, Z denoting linear or branched alkyl, haloalkyl, alkenyl, alkynyl or alkoxyalkyl, each of a maximum of 4 carbon atoms, e.g., 2-chloro-2',6'-diethyl-N-methoxymethylacetanilide, 2-chloro-2',6'-diethyl-N-butoxymethylacetanilide, 2-chloro-2',6'-dimethyl-N-isobutoxymethylacetanilide, 2-chloro-2',6'-dimethyl-N-isopropoxymethylacetanilide, 2-chloro-2'-methyl-6'-ethyl-N-ethoxymethylacetanilide, 2-chloro-2'-methyl-6'-tert.butyl-N-methoxymethylacetanilide, 2-chloro-2'-methyl-6'-tert.butyl-N-butoxymethylacetanilide, 2-bromo-2'-methyl-6'-tert.butyl-N-methoxymethylacetanilide, or —A—O—$R^2$, A denoting an ethylene chain which is unsubstituted or monosubstituted by ethyl or mono- or disubstituted by methyl, and $R^2$ denoting linear or branched alkyl of a maximum of 3 carbon atoms, linear or branched alkenyl of 3 or 4 carbon atoms, or cycloalkyl or cycloalkylmethyl with 3 to 6 carbon atoms in the cycloalkyl ring, especially cyclopropyl and cyclopropylmethyl, e.g., 2-chloro-2'-ethyl-6'-methyl-N-(1-methoxyprop-2-yl)-acetanilide and 2-chloro-2',6'-dimethyl-N-(2-methoxyethyl)-acetanilide. Haloacetanilides of the formula II in which R denotes linear or branched alkyl, alkenyl or alkynyl, each of a maximum of 4 carbon atoms, alkoxycarbonylmethyl of a maximum of 4 carbon atoms in the alkoxy, or 1,3-dioxolan-2-yl-methyl are also suitable, e.g., 2-chloro-N-isopropylacetanilide, 2-chloro-2',6'-diethyl-N-(ethoxycarbonylmethyl)-acetanilide, 2-chloro-2',6'-dimethyl-N-(1,3-dioxolan-2-yl-methyl)-acetanilide, 2-chloro-2',6'-diethyl-N-(isopropoxycarbonylmethyl)-acetanilide, 2-chloro-2'-methyl-6'-ethyl-N-(isopropoxycarbonylmethyl)-acetanilide, 2-chloro-N-butyn-1-yl-3-acetanilide, and 2-chloro-2'-methyl-6'-ethyl-N-propargylacetanilide.

The haloacetanilides of the formula II, and the manufacture thereof, are disclosed in German Laid-Open Applications DE-OS Nos. 1,014,380 and 2,328,340, U.S. Pat. Nos. 3,742,945 and 3,547,620.

The ratio of the active ingredients to each other in the herbicidal agents may vary widely. Thus, combinations may be used which contain from 0.5 to 20 parts by weight of haloacetanilide of the formula II per part by weight of N-azolylmethylhaloacetanilide of the formula I. The ratio selected depends mainly on the spectrum of weeds or grasses to be combated, and possibly also on the development stage of the plants to be combated. The ratio of N-azolylmethylhaloacetanilide of the formula I to haloacetanilide of the formula II is preferably from 1:0.5 to 1:10 parts by weight.

The amount to be applied of the mixture of active ingredients in the herbicidal agents according to the invention is dependent on the type of soil, the plants making up the stand, and on the climatic conditions prevailing where the agents are employed. Generally, the application rates are from 0.1 to 10, preferably 0.5 to 5, kg of active ingredient mixture per hectare.

Suitable crops in which the herbicidal agents according to the invention may be used are essentially those in which the individual active ingredients may be employed, e.g., rape and other cabbages, groundnuts, cotton, Irish potatoes, sugar-beets and, particularly, Indian corn and soybeans.

The herbicidal agents according to the invention may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient mixtures as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient mixture.

Examples of formulations are given below.

I. 20 parts by weight of a mixture of 1 part by weight of 2-chloro-2',6'-dimethyl-N-(pyrazol-1-yl-methyl)-acetanilide and 2 parts by weight of 2-chloro-2',6'-diethyl-N-methoxymethylacetanilide is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient mixture.

II. 20 parts by weight of a mixture of 1 part by weight of 2-chloro-2',6'-dimethyl-N-(pyrazol-1-yl-methyl)-acetanilide and 3 parts by weight of 2-chloro-2'-ethyl-6'-methyl-N-(1'-methoxyyprop-2'-yl)-acetanilide is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient mixture.

III. 3 parts by weight of a mixture of 1 part by weight of 2-chloro-2',6'-dimethyl-N-(pyrazol-1-yl-methyl)-acetanilide and 2 parts by weight of 2-chloro-N-isopropylacetanilide is intimately mixed with 97 parts by weight of particulate kaolin. A dust is obtained containing 3% by weight of the active ingredient mixture.

IV. 20 parts by weight of a mixture of 1 part by weight of 2-chloro-2',6'-dimethyl-N-(pyrazol-1-yl-methyl)-acetanilide and 5 parts by weight of 2-chloro-2',6'-dimethyl-N-(1,3-dioxolan-2-yl-methyl)-acetanilide is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

V. 30 parts by weight of a mixture of 1 part by weight of 2-chloro-2',6'-dimethyl-N-(pyrazol-1-yl-methyl)-acetanilide and 2 parts by weight of 2-chloro-2',6'-diethyl-N-(ethoxycarbonylmethyl)-acetanilide is intimately mixed with a mixture consisting of 92 parts by weight of powdered silical gel and 8 parts by weight of paraffin oil which has been sprayed onto the surface of this silica gel. A formulation of the active ingredient mixture is obtained having good adherence.

The herbicidal agents according to the invention may be mixed and applied together with numerous representatives of other herbicidal or growth-regulating active ingredient groups. Examples of suitable mixture components are diazines, benzothiadiazinones, 2,6-dinitroanilines, N-phenylcarbamates, dicarbamates, thiolcarbamates, halocarboxylic acids, triazines, amides, ureas, diphenyl ethers, triazinones, uracils, benzofuran derivatives, etc. Such combinations broaden the spectrum of action. A number of active ingredients which, when combined with the new herbicidal agents, give mixtures useful for widely varying applications are given below by way of example:

| R | $R^1$ | $R^2$ |
|---|---|---|
|  | $NH_2$ | Cl |
|  | $NH_2$ | Br |
|  | $OCH_3$ | $OCH_3$ |
|  | $-N(CH_3)_2$ | Cl |
| 3-$CF_3$-$C_6H_4$- | $NHCH_3$ | Cl |
| cyclohexyl- | $NH_2$ | Br |
| 3-$CF_3$-$C_6H_4$- | $OCH_3$ | $OCH_3$ |

| R | $R^1$ | $R^2$ | $R^3$ | $R^4$ |
|---|---|---|---|---|
| H | $H_3CSO_2$ | H | $n$-$C_3H_7$ | $n$-$C_3H_7$ |
| H | $F_3C$ | H | $C_2H_5$ | $C_4H_9$ |
| H | $F_3C$ | H | $n$-$C_3H_7$ | $n$-$C_3H_7$ |
| H | $F_3C$ | H | $-CH_2-CH_2Cl$ | $n$-$C_3H_7$ |
| H | $SO_2NH_2$ | H | $n$-$C_3H_7$ | $n$-$C_3H_7$ |
| H | $F_3C$ | H | $n$-$C_3H_7$ | $-CH_2$-cyclopropyl |
| $CH_3$ | $CH_3$ | H | H | $-CH(C_2H_5)_2$ |
| H | $F_3C$ | $NH_2$ | $n$-$C_3H_7$ | $n$-$C_3H_7$ |
| H | $CH_3$ | H | $-CH_2-CH_2-Cl$ | $-CH_2-CH_2-Cl$ |

| R | $R^1$ | $R^2$ |
|---|---|---|
| phenyl- | H | $i$-$C_3H_7$ |
| 3-Cl-phenyl- | H | $i$-$C_3H_7$ |
| phenyl- | H | $-CH(CH_3)-C(O)-NH-C_2H_5$ |
| $i$-$C_3H_7$ | $i$-$C_3H_7$ | $CH_2-CCl=CCl_2$ |
| $i$-$C_3H_7$ | $i$-$C_3H_7$ | $CH_2-CCl=CHCl$ |
| $n$-$C_3H_7$ | $n$-$C_3H_7$ | $C_2H_5$ |
| cyclohexyl- | $C_2H_5$ | $C_2H_5$ |
| sec.-$C_4H_9$ | sec.-$C_4H_9$ | $C_2H_5$ |
| $n$-$C_3H_7$ | $n$-$C_3H_7$ | $n$-$C_3H_7$ |
| $C_2H_5$ | $C_2H_5$ | $-CH_2$-$C_6H_4$-Cl |
| norbornyl- | $C_2H_5$ | $C_2H_5$ |
| $i$-$C_3H_7$ | $i$-$C_3H_7$ |  |

| R | X | Y | $R^1$ |
|---|---|---|---|
| $CH_3$ | Cl | Cl | Na |
| $CHF_2$ | F | F | Na |
| Cl | Cl | Cl | Na |

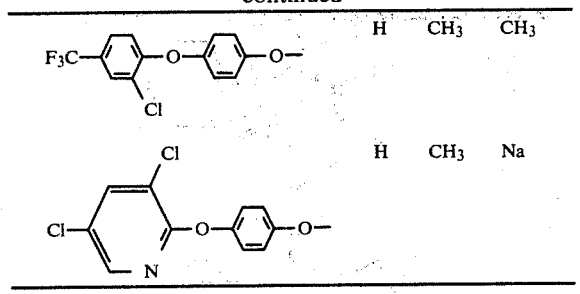
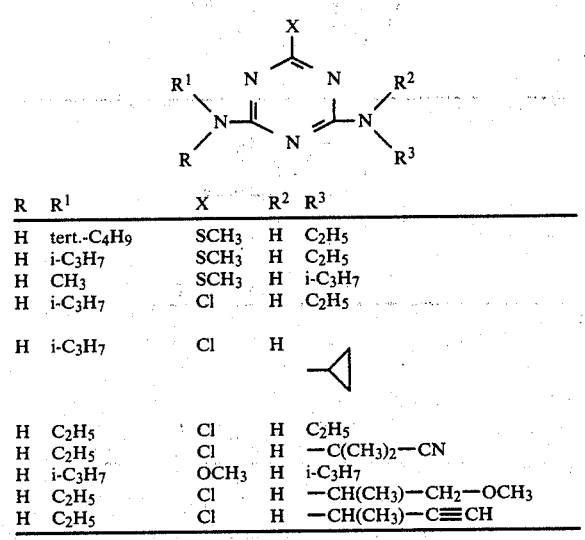
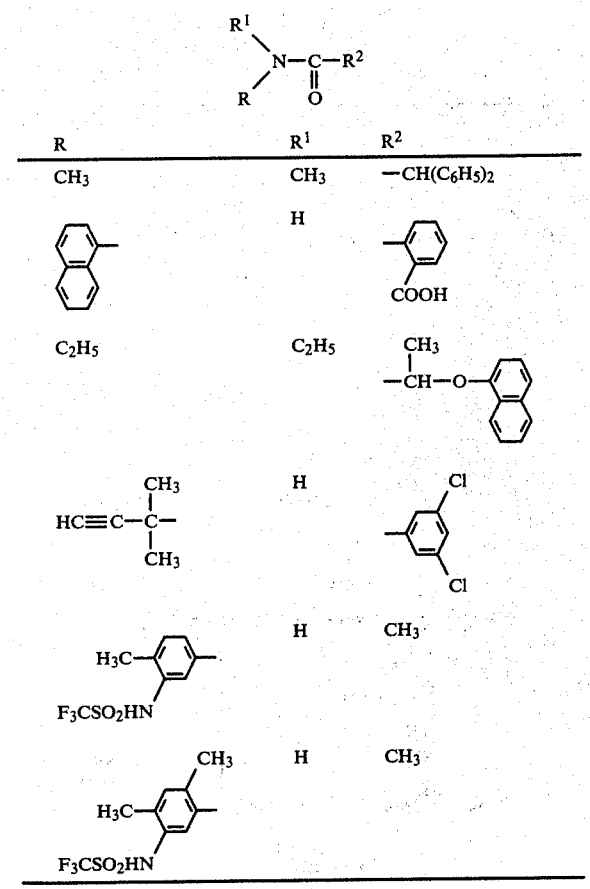

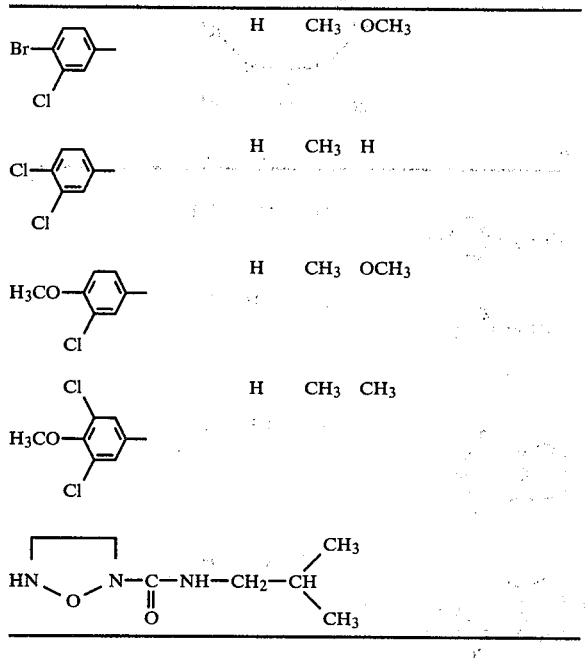
| R | R¹ | R² | R³ |
|---|---|---|---|
| NO₂ | CF₃ | H | H |
| Cl | CF₃ | H | COOH |
| Cl | Cl | H | H |
| Cl | Cl | H | OCH₃ |
| Cl | Cl | H | —C(=O)OCH₃ |
| H | CF₃ | Cl | H |
| H | CF₃ | Cl | OC₂H₅ |
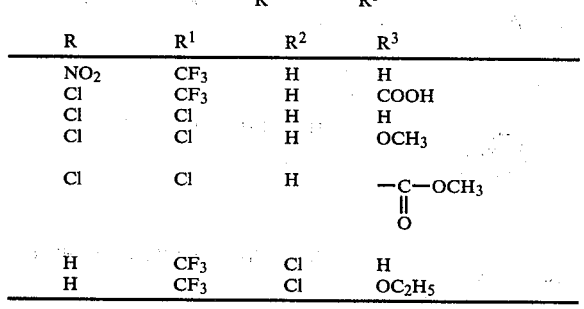
| R | R¹ | R² |
|---|---|---|
| tert.-C₄H₉ | NH₂ | SCH₃ |
| tert.-C₄H₉ | —N=CH—CH(CH₃)CH₃ | SCH₃ |
| phenyl | NH₂ | CH₃ |
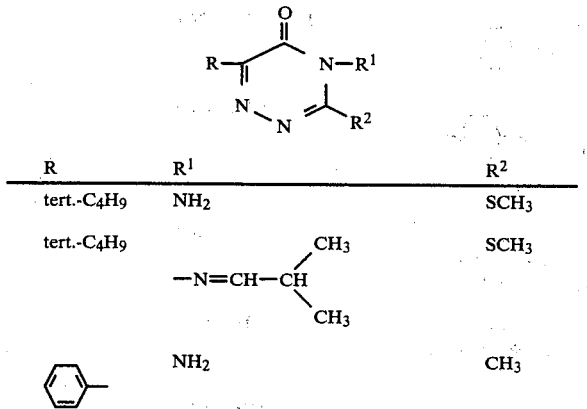
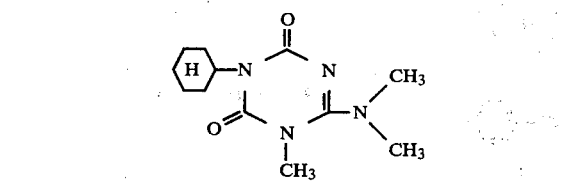
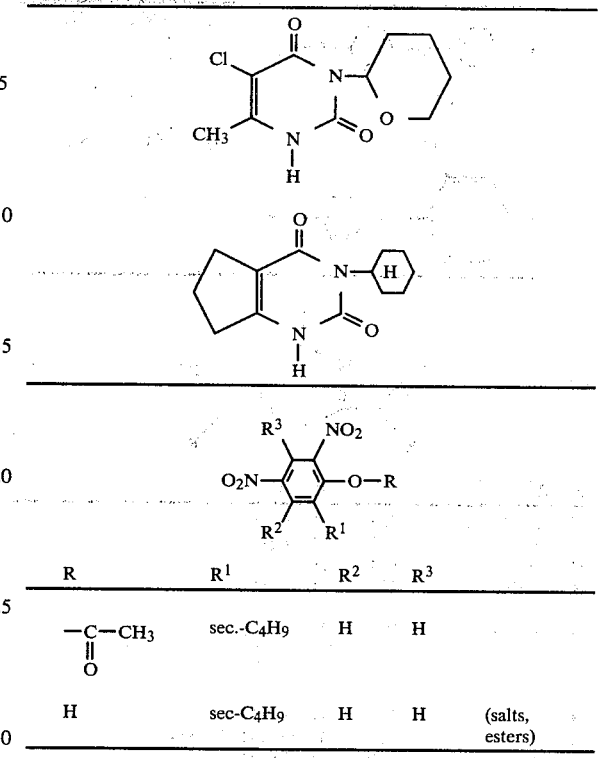
| R | R¹ | R² | R³ | |
|---|---|---|---|---|
| —C(=O)CH₃ | sec.-C₄H₉ | H | H | |
| H | sec-C₄H₉ | H | H | (salts, esters) |
| R | R¹ |
|---|---|
| CH₃ | C₂H₅ |
| (CH₃)₂N— | C₂H₅ |
| (CH₃)(CH₃C(=O))N— | C₂H₅ |
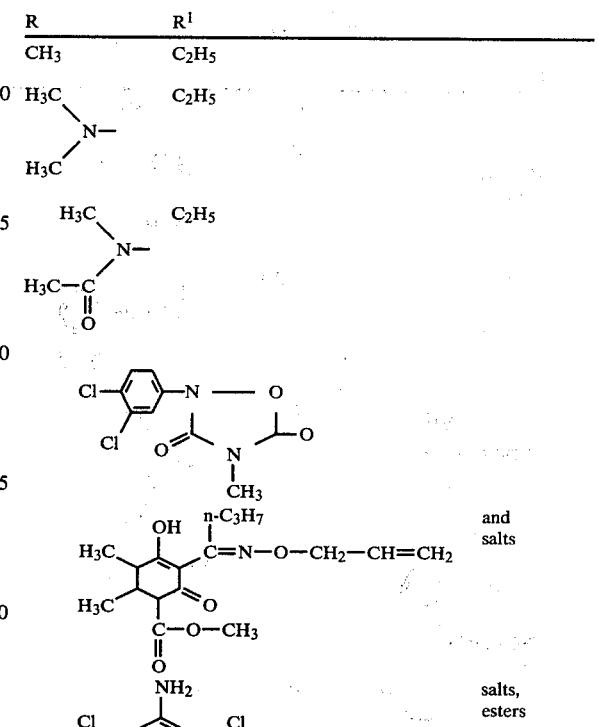
and salts
salts, esters

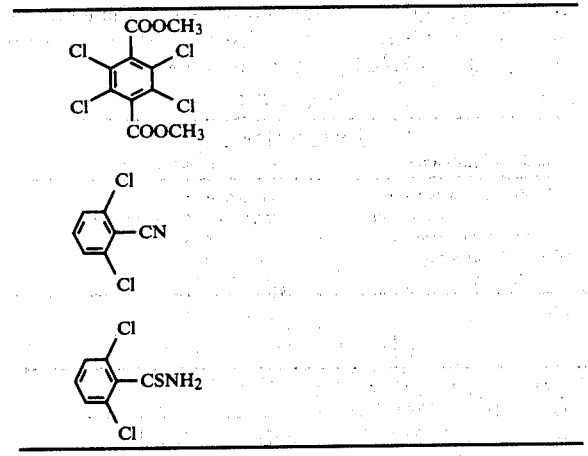
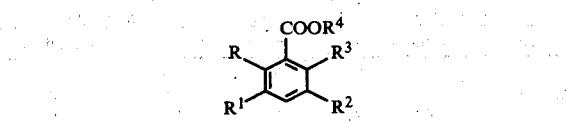

| R | $R^1$ | $R^2$ | $R^3$ | $R^4$ | |
|---|---|---|---|---|---|
| H | Cl | $NH_2$ | Cl | H | (salts, ester, amides) |
| H | I | I | I | H | |
| Cl | H | Cl | $OCH_3$ | H | |

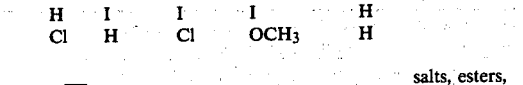

salts, esters, amides

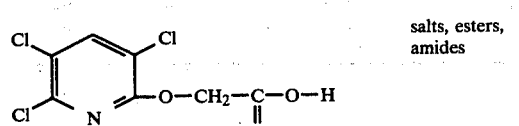

salts, esters, amides

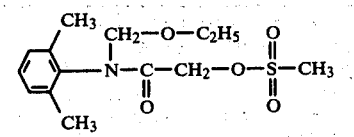

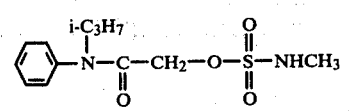

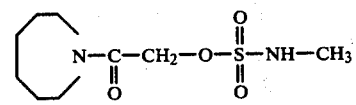

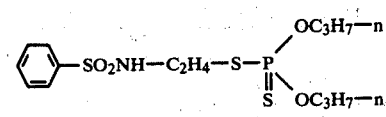

and other salts

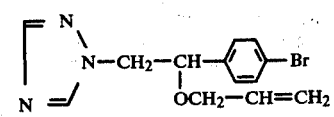

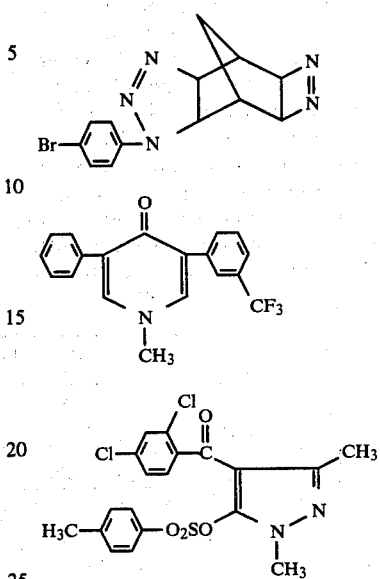

It is also useful to apply the new mixtures according to the invention, either alone or in combination with other herbicides, in admixture with further crop protection agents, e.g., agents for combating pests or phytopathogenic fungi or bacteria. Of interest is also the fact that the new mixtures may also be mixed with mineral solutions used to eliminate nutritional or trace element deficiencies.

The synergistic increase in action achieved by the combined use of haloacetanilides of the formulae I and II in the herbicidal agents according to the invention is demonstrated in the greenhouse experiments and experiments in the open described below.

I. Greenhouse experiments

The vessels were plastic flowerpots having a volume of 300 cm³ and the substrate was a sandy loam containing about 1.5% humus. The seeds of the test plants given in Table 1 were sown shallow, and separated according to species. The individual active ingredients and the mixtures thereof were then applied immediately to the surface of the soil. They were suspended or emulsified in water as vehicle and sprayed through finely distributing nozzles. After treatment, the vessels were lightly sprinkler-irrigated to induce germination and growth and to activate the chemical agents. The vessels were then covered with transparent plastic hoods until the plants had taken root. These hoods ensured uniform germination of the test plants—to the extent that this was not impaired by the chemicals—and prevented readily volatile substances from evaporating.

The pots were placed in either cooler (15° to 30° C.) or warmer (25° to 40° C.) parts of the greenhouse, depending on the temperature requirements of the plants. The experiments were run for from 4 to 6 weeks, during which period the plants were tended and their reaction to the individual treatments was assessed.

II. Experiments in the open

These experiments were run on small plots in loamy sand and loam (pH:6) with a humus content of 1 to 1.5%. Pre-emergence treatment took place either immediately after the crop plants had been sown, or at the latest 3 days later. The crop plants were sown in rows. The weed flora was made up of various species and was naturally occurring. The substances were emulsified or suspended in water as vehicle and applied by means of a motor-driven plot spray mounted on a hitch. Where no rain fell, the plots were sprinkled to ensure normal germination and growth of the crop plants and weeds. All the experiments were run for several weeks, assessment being made at certain intervals during this period.

The following tables contain the compounds examined, the application rates in kg/ha of active ingredient, and the species of test plants. For assessment, the 0 to 100 scale was used, 0 denoting no damage or normal emergence, and 100 denoting no emergence or complete destruction of at least the visible plant parts.

The following active ingredients were employed:
2-chloro-2',6'-dimethyl-N-(pyrazol-1-yl-methyl)-acetanilide (active ingredient A);
2-chloro-2',6'-diethyl-N-(methoxymethyl)-acetanilide (active ingredient B);
2-chloro-2'-ethyl-6'-methyl-N-(1'-methoxyprop-2'-yl)-acetanilide (active ingredient C); and
2-chloro-N-isopropylacetanilide (active ingredient D).

For an arithmetical check of the synergistic action of the mixtures, the action of the individual compounds was ascertained at graduated application rates (dosage-action series). The action theoretically to be expected when two components—the individual actions of which are known—are mixed is calculated from these figures in accordance with the method suggested by F. H. A. Rumens in Weed Science, 23, 4 et seq., 1975. These calculated values were compared with the results actually achieved by the mixtures in the experiments. If the degree of damage is greater than that calculated, the mixture has a synergistic action.

Results

Tables 2, 3 and 4 show that the degree of damage inflicted on the unwanted plants which was actually registered is above that theoretically to be expected. These combinations of active ingredients thus have a synergistic action on unwanted grasses and broadleaved species which goes far beyond the action of their individual active ingredients added together. Particularly the results obtained in the open show that the mixtures according to the invention are suitable for selectively combating unwanted plants in crop plants.

TABLE 1

List of plant names

| Botanical name | Common name |
| --- | --- |
| Alopecurus myosuroides | slender foxtail |
| Chenopodium album | lambsquarters (goosefoot) |
| Sorghum halepense | Jonsongrass |
| Stellaria media | chickweed |
| Zea mays | Indian corn |

TABLE 2

Synergistic herbicidal action of mixtures of active ingredients A and B; preemergence treatment in the greenhouse

| | | Test plants, with theoretical and actual damge | | | | | |
| --- | --- | --- | --- | --- | --- | --- | --- |
| | Appln. rate | Sorghum halepense damage [%] | | Stellaria media damage [%] | | Alopecurus myosuroides damage [%] | |
| Mixture | kg/ha | calc. | ascertained | calc. | ascertained | calc. | ascertained |
| A + B | 0.125 + 0.25 | — | — | 52 | 96 | 44 | 100 |
| A + B | 0.125 + 0.375 | 30 | 95 | 64 | 98 | 53 | 100 |
| A + B | 0.25 + 0.5 | 65 | 100 | 91 | 99 | 78 | 100 |
| A + B | 0.25 + 0.75 | 74 | 100 | 93 | 99 | 83 | 100 |

TABLE 3

Synergistic herbicidal action of mixtures of active ingredients A and C; preemergence treatment in the greenhouse

| | | Test plants, with theoretical and actual damage | | | | | |
| --- | --- | --- | --- | --- | --- | --- | --- |
| | Appln. rate | Sorghum halepense damage [%] | | Stellaria media damage [%] | | Alopecurus myosuroides damage [%] | |
| Mixture | kg/ha | calc. | ascertained | calc. | ascertained | calc. | ascertained |
| A + C | 0.06 + 0.18 | 43 | 96 | 13 | 91 | 56 | 100 |
| | 0.125 + 0.25 | 89 | 96 | 51 | 98 | 81 | 100 |
| | 0.125 + 0.375 | 94 | 100 | 66 | 96 | 84 | 100 |

TABLE 4

Control of Chenopodium album by synergistic mixtures; preemergence application in the open

| | | Test plants, with theoretical and actual damage | | |
| --- | --- | --- | --- | --- |
| | | Chenopodium album damage [%] | | Crop plant - Zea mays damage [%] |
| Mixture | Appln. rate kg/ha | calc. | ascertained | ascertained |
| A + B | 0.125 + 1.5 | 67 | 85 | 0 |
| | 0.25 + 1.5 | 76 | 88 | 0 |
| | 0.5 + 1.5 | 89 | 95 | 0 |
| | 0.5 + 0.5 | 71 | 98 | 0 |
| A + C | 0.25 + 1.5 | 40 | 75 | 0 |
| | 0.5 + 1.5 | 52 | 90 | 0 |
| | 0.25 + 2.0 | 50 | 82 | 0 |
| | 0.5 + 2.0 | 61 | 95 | 2.5 |
| | 0.75 + 0.75 | 58 | 92 | 2.5 |
| A + D | 0.25 + 2.0 | 40 | 75 | 0 |
| | 0.5 + 2.0 | 48 | 88 | 2.5 |

We claim:

1. A herbicidal agent comprising a mixture of 2-chloro-2',6'-dimethyl-N-(3,5-dimethylpyrazol-1-yl-methyl)-acetanilide as compound I and 2-chloro-2',6'-diethyl-N-(methoxymethyl)-acetanilide as compound II, and wherein the weight ratio of I to II is from 1:0.5 to 1:20.

2. The herbicidal agent of claim 1, wherein the weight ratio of I to II is from 1:0.5 to 1:10.

* * * * *